United States Patent
Jang et al.

(10) Patent No.: US 7,846,990 B2
(45) Date of Patent: Dec. 7, 2010

(54) REACTIVE ORGANO-MODIFIED INORGANIC PARTICLES AND BIODEGRADABLE HYBRID MATERIAL CONTAINING THE SAME

(75) Inventors: Guang-Way Jang, Hsinchu (TW); Hsiu-Yu Cheng, Kaohsiung (TW)

(73) Assignee: Industrial Technology Research Institute, Hsinchu (TW)

( * ) Notice: Subject to any disclaimer, the term of this patent is extended or adjusted under 35 U.S.C. 154(b) by 302 days.

(21) Appl. No.: 12/000,860

(22) Filed: Dec. 18, 2007

(65) Prior Publication Data

US 2008/0214697 A1    Sep. 4, 2008

(30) Foreign Application Priority Data

Dec. 21, 2006    (TW) .............................. 95148162 A

(51) Int. Cl.
- *C08K 9/10*  (2006.01)
- *C08K 7/16*  (2006.01)
- *B32B 5/16*  (2006.01)
- *B32B 19/02* (2006.01)
- *B32B 27/14* (2006.01)

(52) U.S. Cl. .................. 523/124; 523/205; 523/223; 428/403; 428/405; 428/407

(58) Field of Classification Search ............... 523/124, 523/205, 223; 428/403, 405, 407
See application file for complete search history.

(56) References Cited

FOREIGN PATENT DOCUMENTS

| | | |
|---|---|---|
| JP | 2001-240769 A | 9/2001 |
| JP | 2001-294423 A | 10/2001 |
| JP | 2006-282582 A | 10/2006 |

*Primary Examiner*—Kriellion A Sanders
(74) *Attorney, Agent, or Firm*—Birch, Stewart, Kolasch & Birch, LLP

(57) ABSTRACT

A reactive organo-modified inorganic particle. Inorganic particles are modified with functional groups through chemical bonding, ionic bonding, hydrogen bond or complex formation. The functional groups of organo-modified inorganic particle can react with monomer or oligomer of biodegradable materials to facilitate crosslinking and functionalization, thus improving physical properties of the inorganic particle-biodegradable hybrid materials.

25 Claims, 6 Drawing Sheets

Al Ka1

Al Ka1

Al Ka1

REACTIVE ORGANO-MODIFIED INORGANIC PARTICLES AND BIODEGRADABLE HYBRID MATERIAL CONTAINING THE SAME

BACKGROUND OF THE INVENTION

1. Field of the Invention

The invention relates to organo-modified inorganic particles, and in particular to organo-modified inorganic particles reactive to biodegradable materials, and a biodegradable hybrid material containing the particles.

2. Description of the Related Art

Current environmental concerns increasingly demand use of environmentally friendly materials such as those implementing biodegradable constituents.

A polymer, plant fiber or inorganic clay is conventionally added to biodegradable materials to enhance thermal stability and mechanical properties thereof, such that the scope of application for the biodegradable material is expanded, such as in fabrication of electronic and photoelectric devices. Irrespective of whether organic or inorganic additives are used, physical properties of the biodegradable material are improved by increasing compatibility of interfaces between the biodegradable material and the additives.

One popular inorganic additive in biodegradable material is clay. A conventional modifier separates the layered structure of clay to make it compatible with organic material. There is no strong bonding in the organic-inorganic interfaces between the conventional modifier and clay. In addition, because of limitations of molecule structure of the biodegradable material, it is difficult to modify or crosslink. The biodegradable material with higher molecule weight requires a longer reaction time. For example, poly lactic acid (PLA) is formed by first forming cyclic lactic acid molecules, followed by polymerization of the cyclic lactic acid molecules by a ring opening polymerization to achieve a high molecule weight of PLA.

Therefore, the invention provides a reactive organo-modified inorganic particle compatible with the biodegradable material to overcome the above problems.

BRIEF SUMMARY OF THE INVENTION

An object of the invention is to modify inorganic particles with an organic modifier. Organic functional groups of the organic modifier are connected to the surfaces of the inorganic particles through chemical bonding, ionic bonding, hydrogen bond or complexation between organic-inorganic interfaces. At least parts of the organic functional groups on the inorganic particles are reactive to a biodegradable material, such that the modified inorganic particles are compatible with the biodegradable material.

Another object of the invention is to react the modified inorganic particles with monomer or oligomer of biodegradable materials to obtain higher molecule weights, and therefore, better physical properties.

The invention provides a reactive organo-modified inorganic particle, comprising an inorganic particle, and at least one organic modifier adsorbed or bonded to the inorganic particle, wherein the at least one organic modifier contains a functional group reactive to a biodegradable material. The at least one organic modifier comprises the formula X—B—Y and optionally further comprises the formula X—B—Y', where X is a functional group adsorbed or bonded to the inorganic particle, B is a central portion of the organic modifier, Y is a functional group reactive to the biodegradable material, and Y' is a functional group non-reactive to the biodegradable material. There is a strong bonding in the organic-inorganic interfaces between the organic modifier and the inorganic particle. In addition, the modified inorganic particle is reactive to the biodegradable material, such that the physical properties of the resulting hybrid are enhanced for wider applications.

The invention also provides a method of fabricating a reactive organo-modified inorganic particle, comprising modifying an inorganic particle with at least one organic modifier by adsorbing or bonding to form the reactive organo-modified inorganic particle, wherein the at least one organic modifier contains a functional group reactive to a biodegradable material. The at least one organic modifier comprises the formula X—B—Y and optionally further comprises the formula X—B—Y', where X is a functional group adsorbed or bonded to the inorganic particle, B is a central portion of the organic modifier, Y is a functional group reactive to the biodegradable material, and Y' is a functional group non-reactive to the biodegradable material.

The invention further provides a biodegradable material/inorganic particle hybrid, comprising a biodegradable material matrix, and a plurality of reactive organo-modified inorganic particles as described, uniformly dispersed in the biodegradable material matrix, wherein chemical bonding is formed between the reactive organo-modified inorganic particles and the biodegradable material matrix.

A detailed description is given in the following embodiments with reference to the accompanying drawings.

BRIEF DESCRIPTION OF THE DRAWINGS

The invention can be more fully understood by reading the subsequent detailed description and examples with references made to the accompanying drawings, wherein.

DETAILED DESCRIPTION OF THE INVENTION

Figure 1:
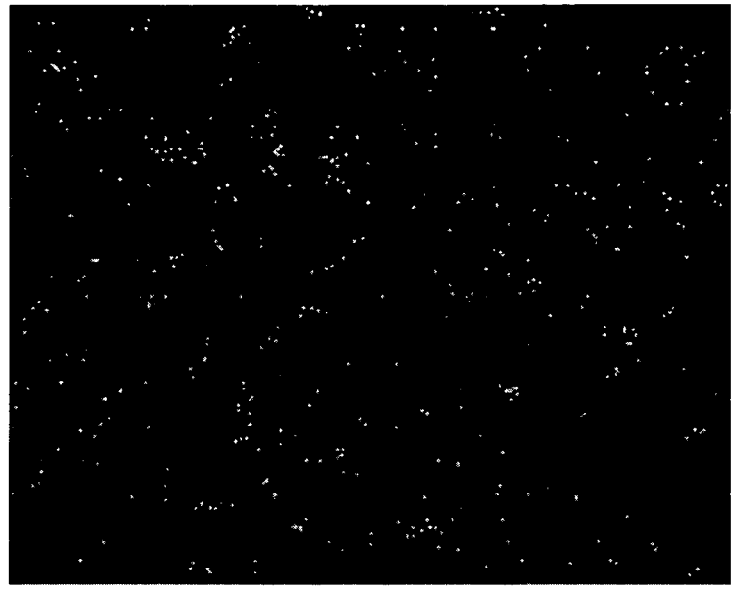
FIG. 1 is a SEM photograph of the biodegradable material/reactive organo-modified inorganic particle hybrid of Example 3.

The following description is of the best-contemplated mode of carrying out the invention. This description is made for the purpose of illustrating the general principles of the invention and should not be taken in a limiting sense. The scope of the invention is best determined by reference to the appended claims.

The invention modifies a surface of an inorganic particle with an organic modifier, such that organic functional groups are adsorbed or bonded thereon. The end groups of organic functional groups comprise functional groups reactive and non-reactive to a biodegradable material.

After an organo-modified inorganic particle of the invention is formed, the modified inorganic particles are mixed into the biodegradable materials or the modified inorganic particles are reacted with monomer or oligomer of biodegradable materials for polymerization. The surface of the organo-modified inorganic particle contains a plurality of reactive functional groups which can co-polymerize with monomer or oligomer of biodegradable materials and catalyze a crosslinking reaction between the biodegradable materials, such that a higher molecule weight of biodegradable material is obtained. In addition to the compatibility with biodegradable material, the organo-modified inorganic particle is further reactive to the biodegradable material.

The biodegradable material can be a polymer of polyester or vinyl, wherein polyester includes poly-glycolic acid (PGA), poly lactic acid (PLA), polycaprolactone (PCL), polyhydroxybutyrate (PHB), polyhydroxybutyrate-valerate (PHBV) or polyhydroxyvalerate (PHV), and vinyl polymer includes polyvinyl acetate (PVAC), poly(butylene succinate) (PBS), polyvinyl alcohol (PVA), or poly-dioxanone (PDS).

The organo-modified inorganic particle according to the invention can be made by inorganic particles reacted with equal molar equivalent of organic modifier, such that surfaces of the inorganic particle have a plurality of organic functional groups thereon. The organic functional groups include functional groups reactive and non-reactive to the biodegradable material.

The inorganic particle can be metal oxide or inorganic layered material, wherein metal oxide has the formula $M_xO_y$ or $MO_{y-a}(OH)_a$, where M is alkaline metal or alkaline-earth metal, such as Si, Al, Ti, Zn, Sr, $Sb_2$, $Rh_2$, Pt, Pb, Sn, Ru, Co, Ag, Cd, Fe, Mn, Cu or Zr etc., $x \geq 1$, $a \leq 8$, $y \geq 1$ and $y \geq a$. Metal Oxide includes $SiO_2$, $Al_2O_3$, $Al(OH)_3$, $Mg(OH)_2$, $SrO_2$, $Sb_2O_3$, ZnO, $TiO_2$ or $ZrO_2$. Inorganic layered material includes mica, smectite clay, vermiculite, halloysite, sericite or talc.

The organic modifier comprises the formula X—B—Y and optionally further comprises the formula X—B—Y'. X is a functional group adsorbed or bonded to the inorganic particle, such as —COOH, —Cl, —OH, —CHOCH$_2$CH$_2$OH, N$^+$, P$^+$ or O$^-$. B is a central portion of the organic modifier, such as —Si—, —(CH)$_n$—, —CO—, —(COCHCH$_3$)$_n$—, —C$_2$H$_4$O—, —(CH$_2$)$_n$—, —C$_6$H$_5$—, or —C$_6$H$_{11}$—, where n is a positive integer. Y is a functional group reactive to the biodegradable material, such as —NH$_2$, —COOH, or —OH. Y' is a functional group non-reactive to the biodegradable material, such as —(CH$_2$)$_m$CH$_3$, or —C$_6$H$_5$, where m is zero or a positive integer.

The structure of the organo-modified inorganic particle according to the invention can comprise:

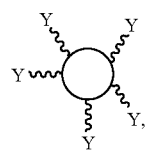

and optionally further comprise

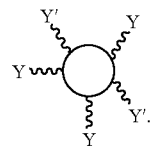

In the above structures, O is the inorganic particle,

~~~ is the organic modifier, Y is a functional group reactive to the biodegradable material, and Y' is a functional group non-reactive to the biodegradable material. In the following description, the organic modifier is represented by

~~~ indicating that the organic modifier may contain a plurality of functional groups with Y and Y'

The organic modifier and the inorganic particle can be connected by chemical bonding, ionic bonding, hydrogen bonding, or complexation, as, for example,
(a) chemical bonding:

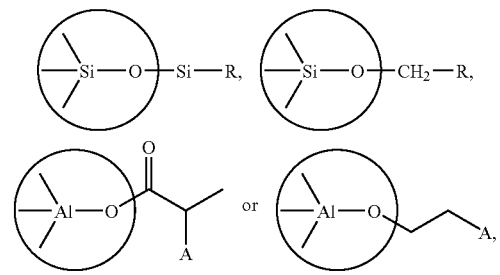

wherein the circle is inorganic particle, A is —COOH, —Cl, —NH$_2$, —OH, R is —H, —CH$_3$, —(CH$_2$)$_n$NH$_2$, —(CH$_2$)$_n$COOH, —(CH$_2$)$_n$CH$_3$, —C$_6$H$_5$, where n is an integer $\geq 1$. Although only one organic group is shown, those skilled in the art will understand that there can be a plurality or more than one type of organic groups on the inorganic particle, such as functional groups reactive and non-reactive to the biodegradable material.

An embodiment of chemical bonding between the organic modifier and the inorganic particle into the organo-modified inorganic particle using 2-chloropropionyl chloride as the organic modifier is shown in:

formula (I)

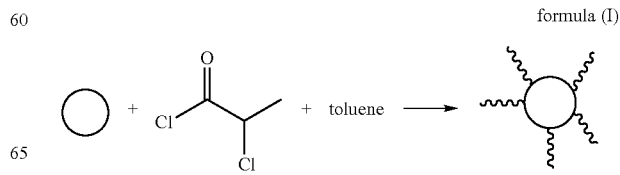

Where O is the inorganic particle, and

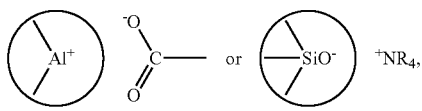

is the organic modifier. As shown, a plurality of organic groups is bonded on surface of the inorganic particle.

(b) ionic bonding:

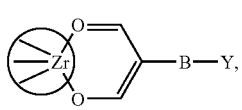

wherein the circle is the inorganic particle, R is —H, —H$_3$, —(CH$_2$)$_n$NH$_2$, —(CH$_2$)$_n$COOH, —(CH$_2$)$_n$CH$_3$, —C$_6$H$_5$, where n is an integer $\geq 1$. Similarly, while only one organic group is shown bonded on the inorganic particle, a plurality or more than one type of organic group may be present on the inorganic particle.

An embodiment of ionic bonding between the organic modifier and the inorganic particle into the organo-modified inorganic particle using lactic acid as the organic modifier is shown as:

formula (II)

is the organic modifier. As shown, a plurality of organic groups is bonded on the surface of the inorganic particle.

(c) complexation:

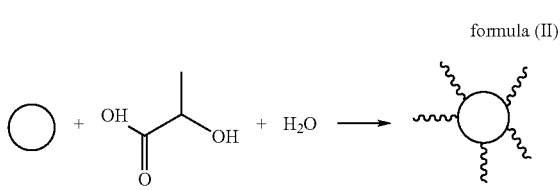

wherein the circle is the inorganic particle, B is —(CH$_2$)$_n$CH$_3$—, —C$_6$H$_5$—, or —C$_6$H$_{11}$—, where n is an integer $\geq 1$, Y is —OH, —COOH, or —NH$_2$. While only one organic group is shown bonded on the inorganic particle, a plurality or more than one type of organic groups may be bonded thereon.

An embodiment of complexation between the organic modifier and the inorganic particle into the organo-modified inorganic particle is shown as:

formula (III)

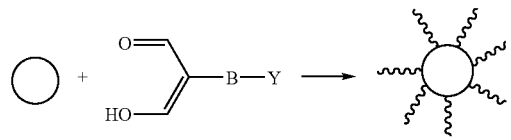

Where O is the inorganic particle, and is the organic modifier. As shown in formula (III), a plurality of organic groups is bonded on the surface of the inorganic particle.

The content of organic groups on the surface of the organo-modified inorganic particle is about 10 to 70 weight percentages of the inorganic particle. When the inorganic particle is metal oxide, the content of organic groups is about 30 to 65 weight percentages of the inorganic particle. When the inorganic particle is clay, the content of organic groups is about 10 to 70 weight percentages of the inorganic particle.

A biodegradable material/inorganic particle hybrid according to the invention can be formed by modified inorganic particles reacting with monomer or oligomer of biodegradable materials or directly mixing the modified inorganic particles into the biodegradable materials. As a result of functional groups reactive to the biodegradable material on surfaces of the organo-modified inorganic particles, for example, —OH, —COOH, or —NH$_2$, the modified inorganic particles are compatible in the biodegradable materials. In addition, the modified inorganic particles can induce crosslinking between the biodegradable materials. Therefore, a higher molecule weight of biodegradable material such as PLA can be obtained according to the invention. There is no need to polymerize cyclic lactic acid molecules by a ring opening polymerization to achieve higher molecule weight. Further, the reaction time can be reduced, and dispersion of the modified inorganic particles in the biodegradable material is more uniform than the non-modified inorganic particles.

In one embodiment, the content of organo-modified inorganic particles is about 1 to 100 weight parts based on 100 weight parts of monomer, oligomer or polymer of biodegradable materials.

The biodegradable material/inorganic particle hybrid according to the invention has more crystallization than a conventional biodegradable material/non-modified inorganic particle hybrid. As a result of crystallization, the mechanical properties and heat-resistant of the biodegradable material/inorganic particle hybrid of the invention are improved over the conventional biodegradable material/non-modified inorganic particle hybrid. Heat-resistance of the biodegradable material/inorganic particle hybrid of the invention is higher than the conventional biodegradable material/non-modified inorganic particle hybrid, about 30° C. The melting point of the biodegradable material/inorganic particle hybrid of the invention is higher than the conventional biodegradable material/non-modified inorganic particle hybrid about 5° C. In addition, the molecular weight of the biodegradable material/inorganic particle hybrid of the invention is higher than the conventional biodegradable material/non-modified inorganic particle hybrid. The dispersion of the inorganic particles in the biodegradable material according to the invention is better than the dispersion of conventional non-modified inorganic particles, and less aggregation of inorganic particles than the conventional non-modified inorganic particles.

In an embodiment of the invention, the inorganic particles are metal oxide. The particle size of metal oxide is smaller than clay, such that the optical property of biodegradable material/metal oxide hybrid is better.

EXAMPLE 1

Organo-Modified Inorganic Particles with Ionic-Bonding 1 g of an organic modifier of lactic acid and 5 g of inorganic particles of $Al(OH)_3$ were placed with a solvent of water in a reaction vase. The mixture was stirred at room temperature for reaction for 1 hour, and then dried by centrifugation and heat to obtain organo-modified inorganic particles.

EXAMPLE 2

Organo-Modified Inorganic Particles with Chemical Bonding 0.5 g of an organic modifier of 2-chloropropionyl chloride and 0.5 g of inorganic particles of $Al(OH)_3$ were placed with a solvent of toluene in a reaction vase. The mixture was stirred at room temperature for reaction for 4 hours to obtain organo-modified inorganic particles.

EXAMPLE 3

Biodegradable Material/Organo-Modified Inorganic Particle Hybrid 5 g of organo-modified inorganic particles of Example 1 and 100 g of biodegradable material of polylactic acid were placed in a reaction vase. The mixture was stirred at 15 to 100 rpm, 150~220° C. for hybridization to obtain a polylactic acid/organo-modified inorganic particle hybrid. The content of organo-modified inorganic particles can be adjusted to more than twice that described. The hybrid was formed into a film by thermal pressing, and the film observed by scanning electron microscope (SEM) to determine the dispersion of inorganic particles in the biodegradable material. The SEM photograph of polylactic acid/organo-modified inorganic particle hybrid film is shown in FIG. 1. As shown in FIG. 1, the organo-modified inorganic particles dispersed uniformly in the biodegradable material. There was no aggregation of inorganic particles.

Figure 4:
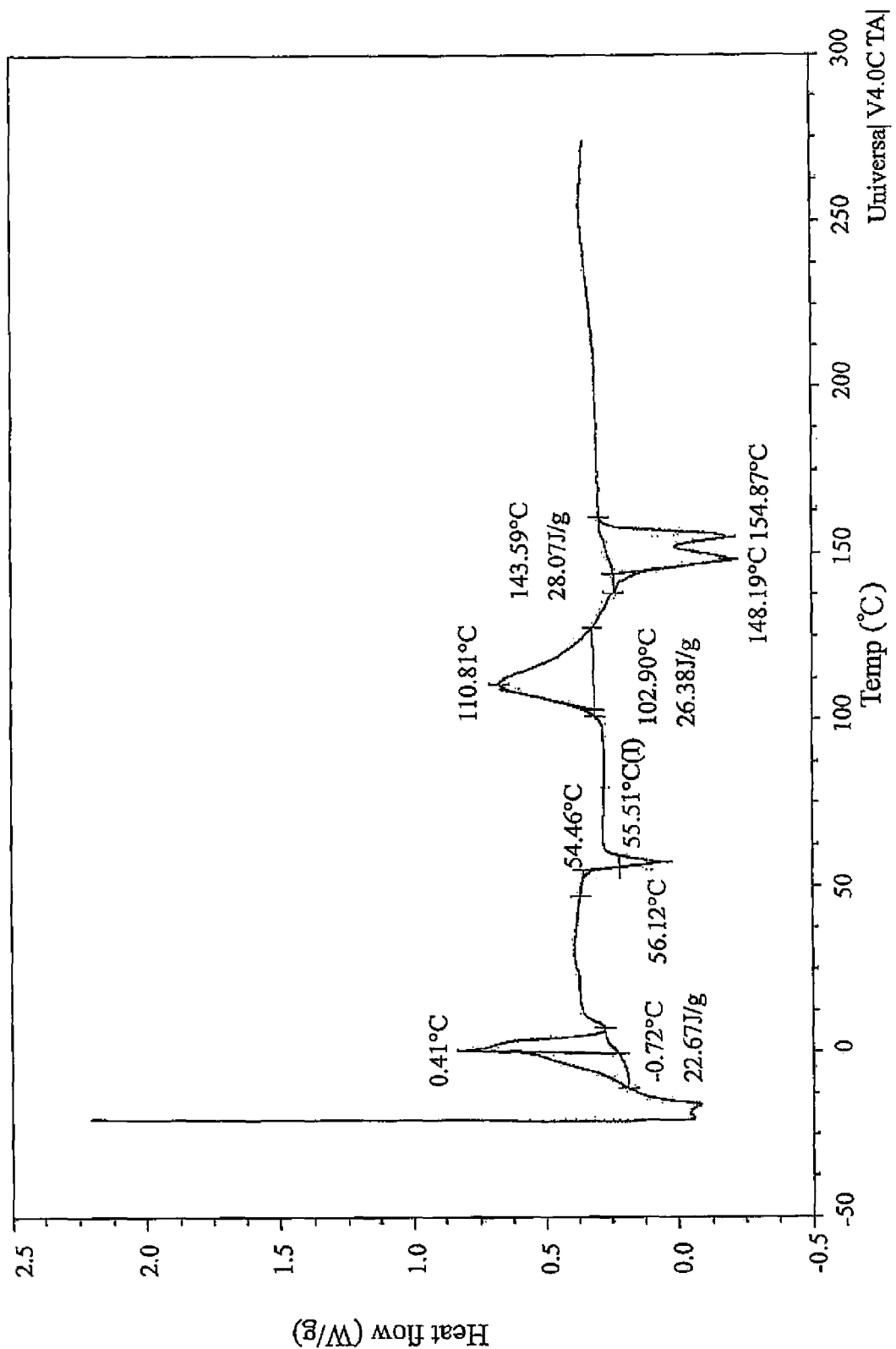
FIG. 4 is a plot of DSC measurement of the biodegradable material/reactive organo-modified inorganic particle hybrid of Example 3.
Figure 6:
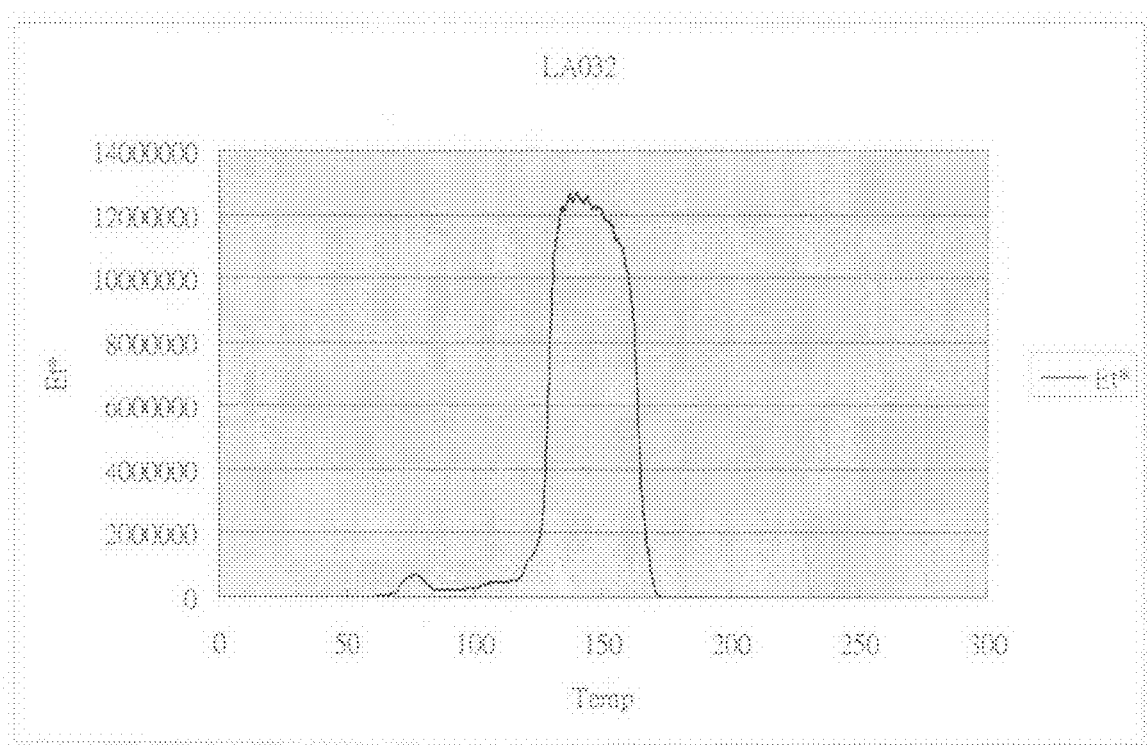
FIG. 6 is a plot of rheometer measurement of the biodegradable material/reactive organo-modified inorganic particle hybrid of Example 3.

In addition, the hybrid was measured by differential scanning calorimetry (DSC), and the result thereof is shown in FIG. 4. As shown in FIG. 4, there was a crystalline peak at 110.8° C. that represents the hybrid crystallizing, and also from FIG. 4, the melting point of the hybrid is seen to be about 155° C. The hybrid was measured by rheometry, and the result thereof is shown in FIG. 6. As shown in FIG. 4, the thermal deforming temperature is about 160° C.

EXAMPLE 4

Figure 2:
FIG. 2 is a SEM photograph of the biodegradable material/reactive organo-modified inorganic particle hybrid of Example 4.

Biodegradable Material/Organo-Modified Inorganic Particle Hybrid 5 g of organo-modified inorganic particles of Example 2 and 100 g of biodegradable material of polylactic acid were placed in a reaction vase. The mixture was stirred at 15 to 100 rpm, 150~220° C. for hybridization to obtain a polylactic acid/organo-modified inorganic particle hybrid. The hybrid was formed into a film by thermal pressing, and observed by SEM to obtain the dispersion of inorganic particles in the biodegradable material. The SEM photograph thereof is shown in FIG. 2. As shown in FIG. 2, the organo-modified inorganic particle dispersed uniformly in the biodegradable material. There was no aggregation of inorganic particles.

COMPARATIVE EXAMPLE 1

Figure 3:
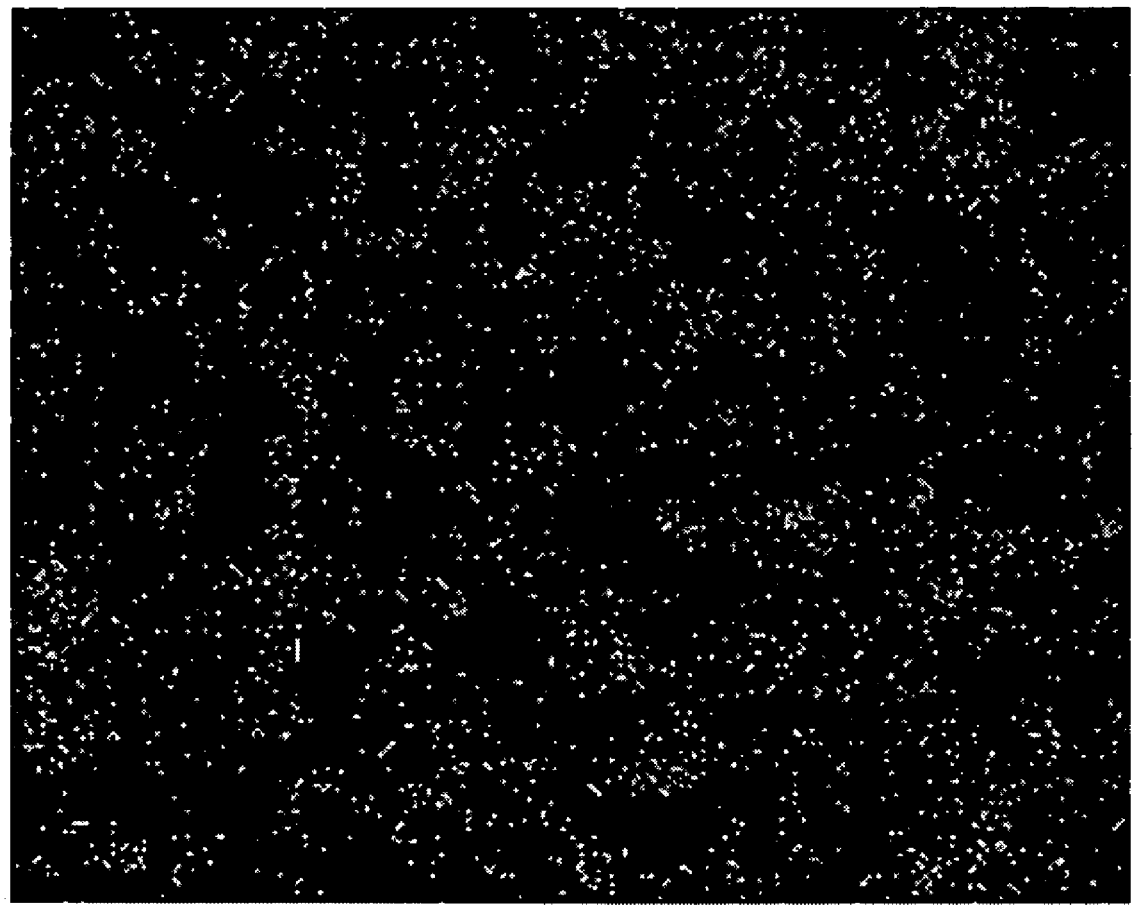
FIG. 3 is a SEM photograph of the biodegradable material/non-modified inorganic particle hybrid of Comparative Example 1.

Biodegradable Material/Non-Modified Inorganic Particle Hybrid 5 g of inorganic particles of $Al(OH)_3$ and 100 g of biodegradable material of polylactic acid were placed in a reaction vase. The mixture was stirred for hybridization to obtain a polylactic acid/non-modified inorganic particle hybrid. The hybrid was formed into a film by thermal pressing and the film observed by SEM to obtain the dispersion of inorganic particles in the biodegradable material. The SEM photograph thereof is shown in FIG. 3. As shown in FIG. 3, the dispersion of non-modified inorganic particles in the biodegradable material was reduced.

Figure 5:
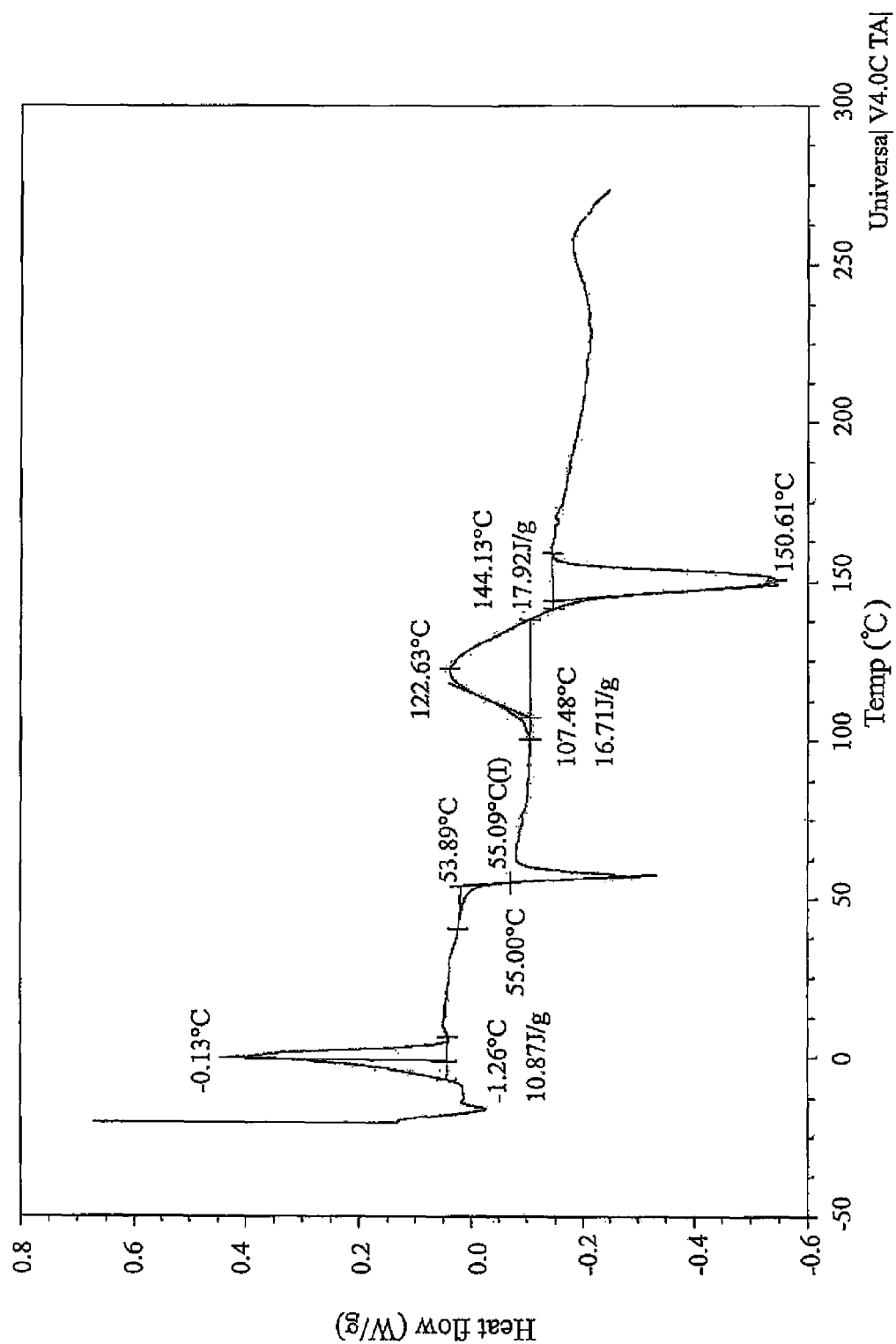
FIG. 5 is a plot of DSC measurement of the biodegradable material/non-modified inorganic particle hybrid of Comparative Example 1.

In addition, the hybrid was measured by DSC, and the result thereof is shown in FIG. 5. As shown in FIG. 5, the melting point of the hybrid is about 150° C.

Figure 7:
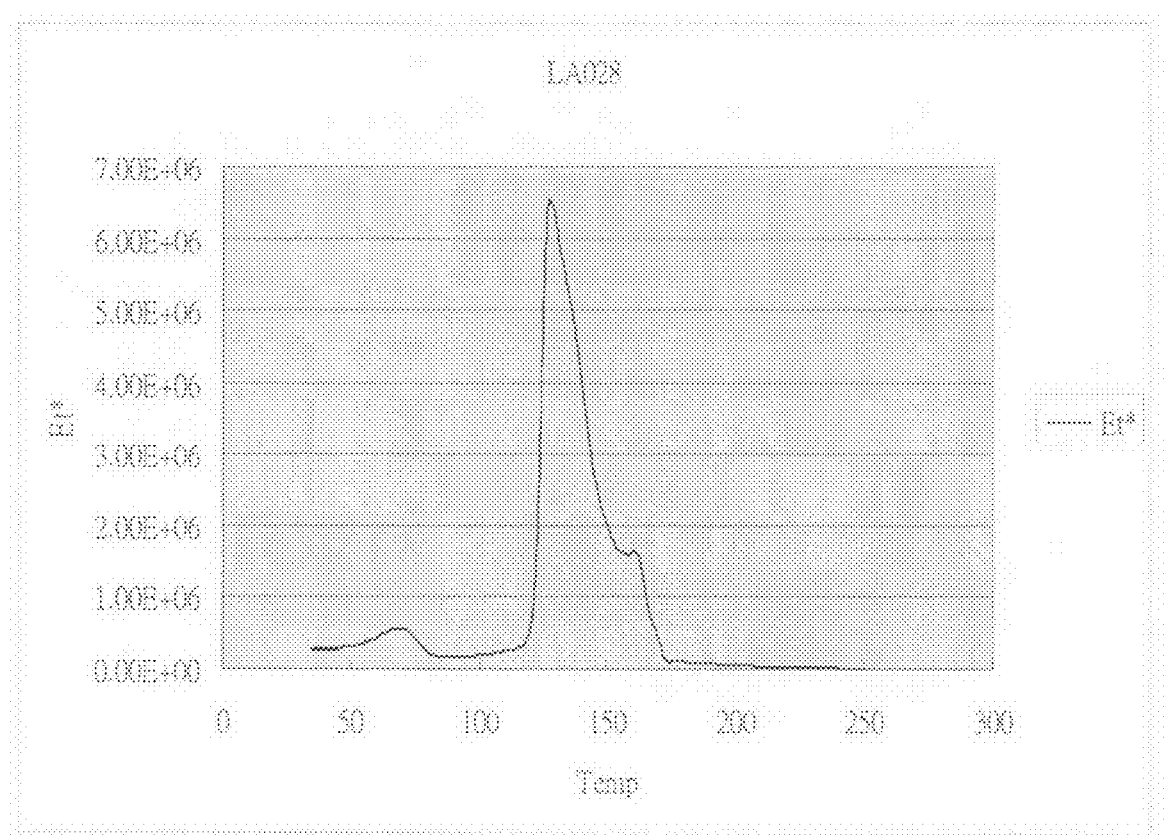
FIG. 7 is a plot of rheometer measurement of the biodegradable material/non-modified inorganic particle hybrid of Comparative Example 1.

The hybrid was measured by rheometry, and the result thereof is shown in FIG. 7. As shown in FIG. 7, the thermal deforming temperature is about 128° C.

Comparison of the SEM photographs of FIGS. 1, 2 and 3 shows improved dispersion of the reactive organo-modified inorganic particles in the biodegradable material according to the invention was compared with non-modified inorganic particles.

From comparing the DSC measured results of FIGS. 4 and 5, the addition of the non-modified inorganic particles into polylactic acid can make the hybrid crystallize because polylactic acid cannot crystallize, but the heat-resistance thereof is reduced. The polylactic acid/reactive organo-modified inorganic particle hybrid according to the invention is not only crystalline but also the melting point thereof is higher than the polylactic acid/non-modified inorganic particle hybrid about 5° C. Because the polylactic acid/reactive organo-modified inorganic particle hybrid according to the invention is crystalline, the mechanical properties thereof are enhanced. The tensile strength of the hybrid of the invention exceeds that of the polylactic acid/non-modified inorganic particle hybrid about 24.04 Kgf.

From the measured results of rhrometry of FIGS. 6 and 7, the thermal deforming temperature of the polylactic acid/ reactive organo-modified inorganic particle hybrid according to the invention exceeds that of the polylactic acid/non-modified inorganic particle hybrid about 32° C. The addition of the reactive organo-modified inorganic particles of the invention can enhance heat-resistant and stability of polylactic acid matrix, such that the scope of applications thereof is expanded and it is suitable for materials of the element used at higher temperature.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A reactive organo-modified inorganic particle, comprising:
   an inorganic particle; and
   at least one organic molecular modifier adsorbed or bonded to the inorganic particle, wherein the at least one organic molecular modifier contains a functional group reactive to a biodegradable material, wherein the at least one organic molecular modifier comprises the formula X—B—Y and optionally further comprises the formula X—B—Y', where X is a functional group adsorbed or bonded to the inorganic particle, B is a central portion of the organic molecular modifier, Y is a functional group reactive to the biodegradable material, and Y' is a functional group non-reactive to the biodegradable material.

2. The reactive organo-modified inorganic particle as claimed in claim 1, wherein X comprises —COOH, —Cl, —OH, —CHOCH$_2$CH$_2$OH, N$^+$,P$^+$ or O$^-$.

3. The reactive organo-modified inorganic particle as claimed in claim 1, wherein B comprises —Si—, —(CH)$_n$—, —CO—, —(COCHCH$_3$)$_n$—, —C$_2$H$_4$O—, —(CH$_2$)$_n$—, —C$_6$H$_5$—, or —C$_6$H$_{11}$—, where n is a positive integer.

4. The reactive organo-modified inorganic particle as claimed in claim 1, wherein Y comprises —NH$_2$, —COOH, or —OH.

5. The reactive organo-modified inorganic particle as claimed in claim 1, wherein Y' comprises —(CH$_2$)$_m$CH$_3$, or —C$_6$H$_5$, where m is zero or a positive integer.

6. The reactive organo-modified inorganic particle as claimed in claim 1, wherein the inorganic particle comprises metal oxide or inorganic layered material.

7. The reactive organo-modified inorganic particle as claimed in claim 6, wherein the metal oxide has the formula M$_x$O$_y$ or MO$_{y-a}$(OH)$_a$, where M is alkaline metal or alkaline-earth metal, $x \geq 1, a \leq 8, y \geq 1$ and $y \geq a$.

8. The reactive organo-modified inorganic particle as claimed in claim 7, wherein the metal oxide comprises SiO$_2$, Al$_2$O$_3$, Al(OH)$_3$, Mg(OH)$_2$, SrO$_2$, Sb$_2$O$_3$, ZnO, TiO$_2$ or ZrO$_2$.

9. The reactive organo-modified inorganic particle as claimed in claim 6, wherein the inorganic layered material comprises mica, smectite clay, vermiculite, halloysite, sericite or talc.

10. The reactive organo-modified inorganic particle as claimed in claim 1, wherein the biodegradable material comprises polyester or vinyl polymer.

11. The reactive organo-modified inorganic particle as claimed in claim 1, wherein an interaction between the organic molecular modifier and the inorganic particle comprises chemical bonding, ionic bonding, complexation, or hydrogen bonding.

12. A method of fabricating a reactive organo-modified inorganic particle, comprising:
    modifying an inorganic particle with at least one organic molecular modifier by adsorbing or bonding to form the reactive organo-modified inorganic particle, wherein the at least one organic molecular modifier contains a functional group reactive to a biodegradable material, wherein the at least one organic molecular modifier comprises the formula X—B—Y and optionally further comprises the formula X—B—Y', where X is a functional group adsorbed or bonded to the inorganic particle, B is a central portion of the organic molecular modifier, Y is a functional group reactive to the biodegradable material, and Y' is a functional group non-reactive to the biodegradable material.

13. The method as claimed in claim 12, wherein X comprises —COOH, —Cl, —OH, —CHOCH$_2$CH$_2$OH, N$^+$,P$^+$ or O$^-$.

14. The method as claimed in claim 12, wherein B comprises —Si—, —(CH)$_n$—, —CO—, —(COCHCH$_3$)$_n$—, —C$_2$H$_4$O—, —(CH$_2$)$_n$—, —C$_6$H$_5$—, or —C$_6$H$_{11}$—, where n is a positive integer.

15. The method as claimed in claim 12, wherein Y comprises —NH$_2$, —COOH, or —OH.

16. The method as claimed in claim 12, wherein Y' comprises —(CH$_2$)$_m$CH$_3$, or —C$_6$H$_5$, where m is zero or a positive integer.

17. The method as claimed in claim 12, wherein the inorganic particle comprises metal oxide or inorganic layered material.

18. The method as claimed in claim 12, wherein the biodegradable material comprises polyester or vinyl polymer.

19. The method as claimed in claim 12, wherein an interaction between the organic molecular modifier and the inorganic particle comprises chemical bonding, ionic bonding, complexation, or hydrogen bonding.

20. A biodegradable material/ inorganic particle hybrid, comprising:
    a biodegradable material matrix; and
    a plurality of reactive organo-modified inorganic particles as claimed in claim 1 uniformly dispersed in the biodegradable material matrix, wherein a chemical bonding is formed between the reactive organo-modified inorganic particles and the biodegradable material matrix.

21. The hybrid as claimed in claim 20, wherein the reactive organo-modified inorganic particles comprise functional groups reactive and non-reactive to the biodegradable material matrix.

22. The hybrid as claimed in claim 21, wherein the functional groups reactive to the biodegradable material matrix comprise —NH$_2$, —COOH, or —OH.

23. The hybrid as claimed in claim 20, wherein the biodegradable material matrix comprises polyester or vinyl polymer.

24. The hybrid as claimed in claim 23, wherein the polyester comprises poly-glycolic acid (PGA), poly lactic acid (PLA), polycaprolactone (PCL), polyhydroxybutyrate (PHB), polyhydroxybutyrate-valerate (PHBV) or polyhydroxyvalerate (PHV).

25. The hybrid as claimed in claim 23, wherein the vinyl polymer comprises polyvinyl acetate (PVAC), poly(butylene succinate) (PBS), polyvinyl alcohol (PVA), or poly-dioxanone (PDS).

* * * * *